(12) United States Patent
Torrini et al.

(10) Patent No.: US 10,649,729 B2
(45) Date of Patent: *May 12, 2020

(54) AUDIO DEVICE WITH AUDITORY SYSTEM DISPLAY AND METHODS FOR USE THEREWITH

(71) Applicants: Antonio Torrini, Austin, TX (US); Daniele Limoni, Castiglion Fiorentino (IT)

(72) Inventors: Antonio Torrini, Austin, TX (US); Daniele Limoni, Castiglion Fiorentino (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/158,537

(22) Filed: Oct. 12, 2018

(65) Prior Publication Data
US 2019/0042189 A1 Feb. 7, 2019

Related U.S. Application Data

(63) Continuation of application No. 15/099,280, filed on Apr. 14, 2016, now Pat. No. 10,108,395.

(51) Int. Cl.
*G06F 3/0482* (2013.01)
*G06F 3/16* (2006.01)
*A61B 5/12* (2006.01)
*G10L 21/038* (2013.01)

(52) U.S. Cl.
CPC ............ *G06F 3/167* (2013.01); *A61B 5/125* (2013.01); *G06F 3/0482* (2013.01); *G06F 3/165* (2013.01); *G10L 21/038* (2013.01)

(58) Field of Classification Search
CPC ........ G06F 3/167; G06F 3/0482; G06F 3/165; G10L 21/038
See application file for complete search history.

(56) References Cited

U.S. PATENT DOCUMENTS

| 6,493,291 | B2* | 12/2002 | Nagano ............ G11B 20/10527 |
| | | | 369/7 |
| 7,164,076 | B2* | 1/2007 | McHale ................. G10H 1/368 |
| | | | 434/307 A |
| 2003/0237043 | A1* | 12/2003 | Novak ............... G06F 17/30017 |
| | | | 715/202 |
| 2004/0117730 | A1* | 6/2004 | Ibrahim ............... G11B 27/034 |
| | | | 715/203 |
| 2004/0264917 | A1* | 12/2004 | Braun .................... G10H 1/368 |
| | | | 386/201 |
| 2005/0091107 | A1* | 4/2005 | Blum ................ G06F 17/30029 |
| | | | 705/14.65 |

(Continued)

*Primary Examiner* — Rashawn N Tillery
(74) *Attorney, Agent, or Firm* — Garlick & Markison; Bruce E. Stuckman

(57) ABSTRACT

Various embodiments include, for example, an audio device that operates by selecting one of a plurality of audio files in response to user interaction with a graphical user interface. The selected one of the plurality of audio files is decoded to generate audio output signals for playback of the selected one of the plurality of audio files via an audio output device. Animated auditory system display data is generated in response to the selected one of the plurality of audio files for display via a display device, wherein the animated auditory system display data animates action of at least one simulated cochlea in response to the selected one of the plurality of audio files. Other embodiments are disclosed.

20 Claims, 15 Drawing Sheets

(56) References Cited

U.S. PATENT DOCUMENTS

| | | | |
|---|---|---|---|
| 2005/0188310 A1* | 8/2005 | Dideriksen | G11B 27/10 715/728 |
| 2005/0190199 A1* | 9/2005 | Brown | G09B 15/00 345/600 |
| 2005/0234983 A1* | 10/2005 | Plastina | G06F 17/30247 |
| 2006/0156906 A1* | 7/2006 | Haeker | G10H 1/0008 84/609 |
| 2006/0218294 A1* | 9/2006 | Rosenberg | H04L 12/1859 709/231 |
| 2006/0218505 A1* | 9/2006 | Compton | G06F 17/30026 715/781 |
| 2006/0274144 A1* | 12/2006 | Landschaft | H04M 19/04 348/14.01 |
| 2007/0100787 A1* | 5/2007 | Lim | G06F 17/30781 |
| 2007/0130514 A1* | 6/2007 | Matthee | G06F 17/211 715/210 |
| 2007/0219937 A1* | 9/2007 | Lee | G11B 27/10 |
| 2011/0096073 A1* | 4/2011 | Adhikari | G06T 15/005 345/426 |
| 2013/0167026 A1* | 6/2013 | Shafer | G06F 3/0484 715/716 |
| 2014/0035920 A1* | 2/2014 | Duwenhorst | G06T 11/001 345/440 |
| 2015/0147737 A1* | 5/2015 | Truncale | G09B 23/32 434/270 |
| 2015/0205570 A1* | 7/2015 | Johnston | G06F 3/165 715/716 |

\* cited by examiner

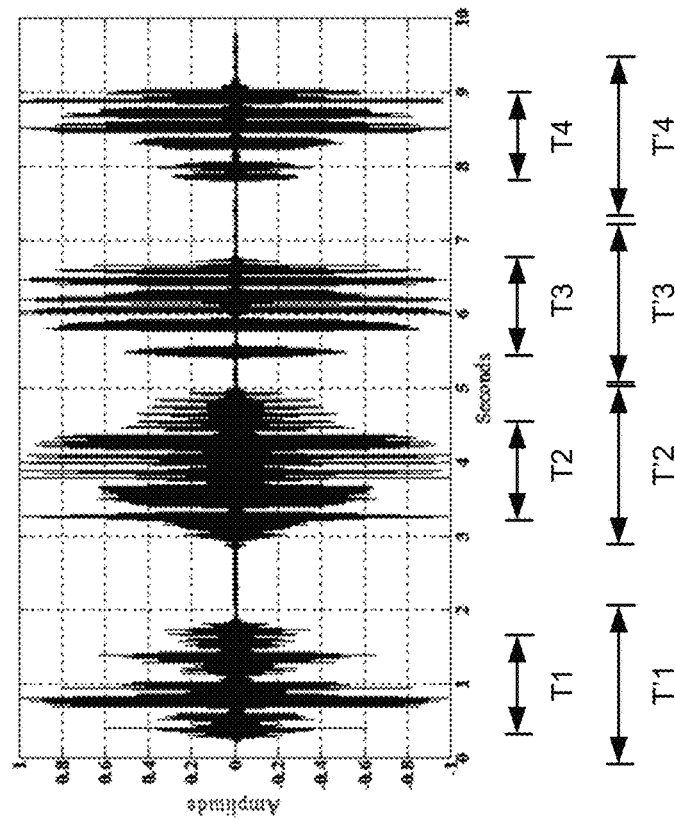
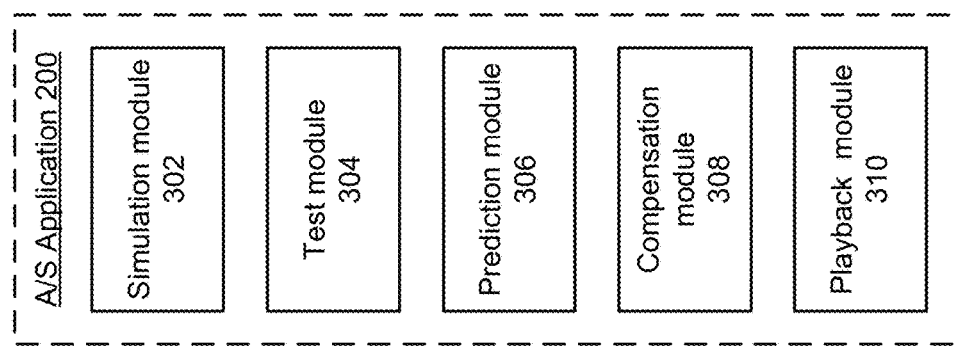

400

600

700

900

1100

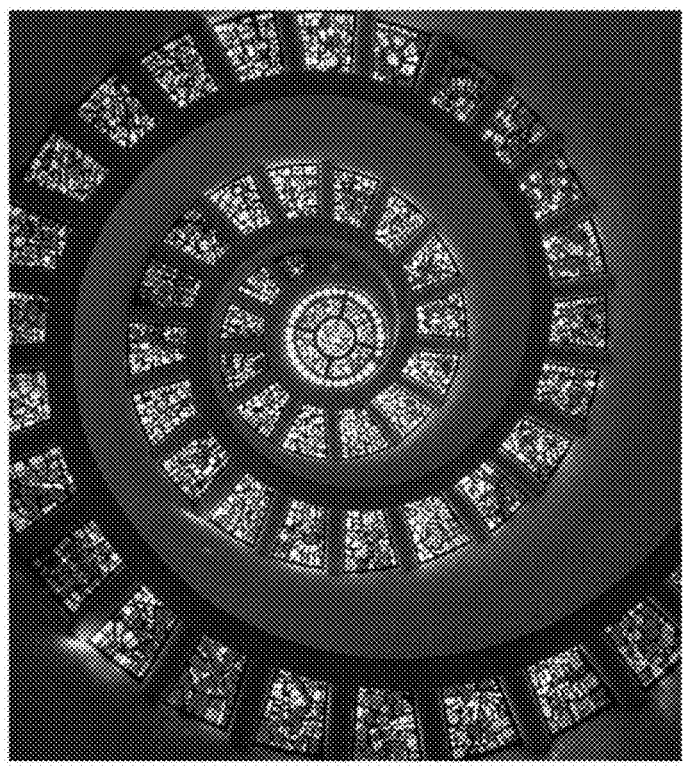
1450
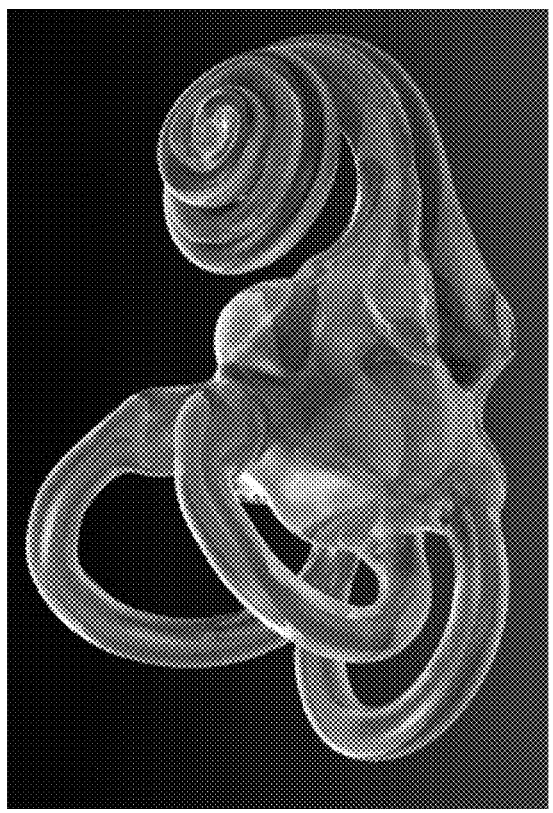
1400
FIG. 14

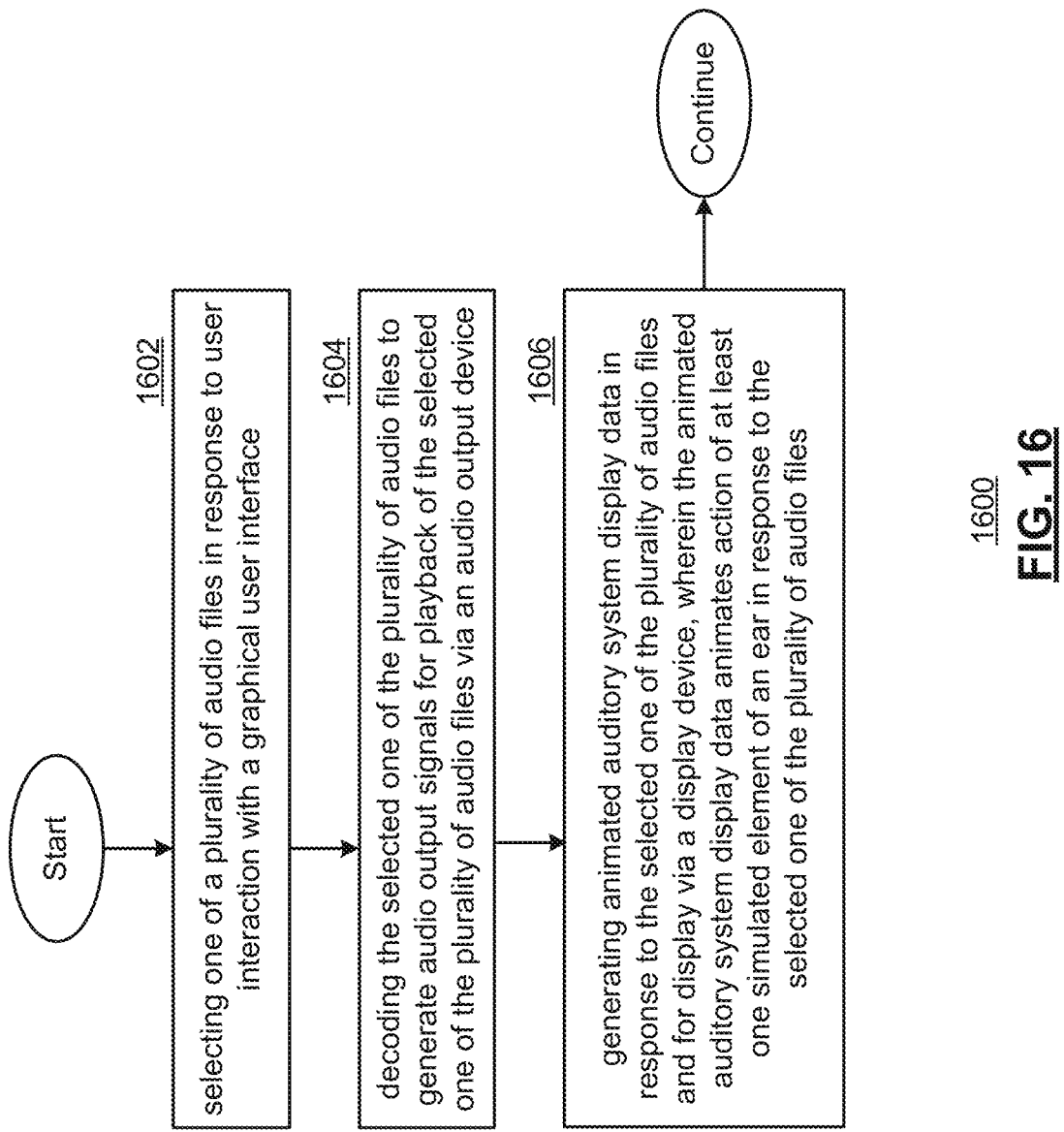

AUDIO DEVICE WITH AUDITORY SYSTEM DISPLAY AND METHODS FOR USE THEREWITH

CROSS REFERENCE TO RELATED APPLICATIONS

The present U.S. Utility patent application claims priority pursuant to 35 U.S.C. § 120 as a continuation of U.S. Utility application Ser. No. 15/099,280, entitled "AUDIO DEVICE WITH AUDITORY SYSTEM DISPLAY AND METHODS FOR USE THEREWITH", filed Apr. 14, 2016, which is hereby incorporated herein by reference in its entirety and made part of the present U.S. Utility patent application for all purposes.

TECHNICAL FIELD OF THE INVENTION

The present invention relates to audio devices with graphical displays and audio playback.

BRIEF DESCRIPTION OF THE SEVERAL VIEWS OF THE DRAWINGS

FIG. 3A presents a block diagram representation of an auditory simulation application in accordance with an embodiment of the present invention.

FIG. 3B presents a graphical diagram representation of an audio signal in accordance with an embodiment of the present invention.

FIG. 14 presents a pictorial representation of cochlear images in accordance with an embodiment of the present invention.

FIG. 16 presents a flow diagram representation of a method in accordance with an embodiment of the present invention.

Figure 2:
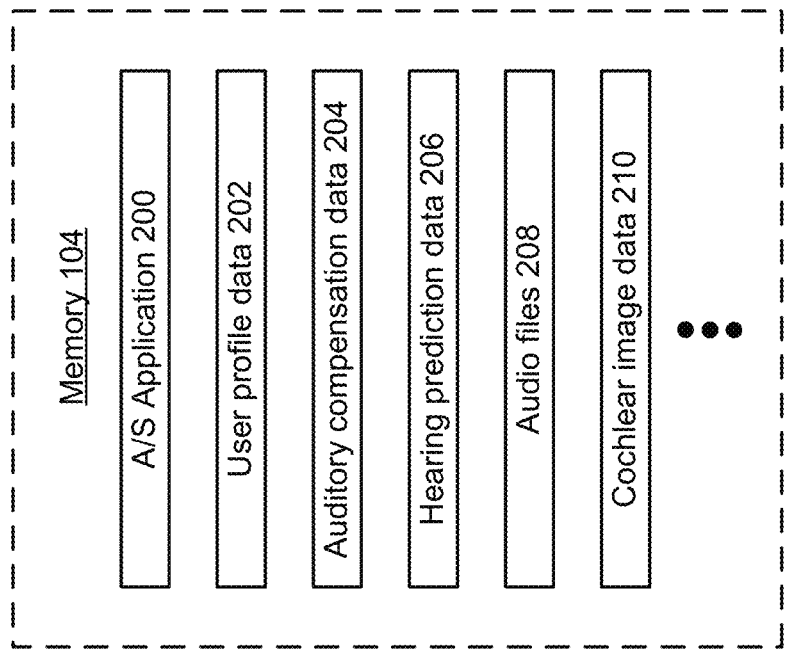
FIG. 2 presents a block diagram of a memory in accordance with an embodiment of the present invention.

DETAILED DESCRIPTION OF THE INVENTION INCLUDING THE PRESENTLY PREFERRED EMBODIMENTS

One or more embodiments are now described with reference to the drawings, wherein like reference numerals are used to refer to like elements throughout. In the following description, for purposes of explanation, numerous details are set forth in order to provide a thorough understanding of the various embodiments. It is evident, however, that the various embodiments can be practiced without these details.

Figure 1:
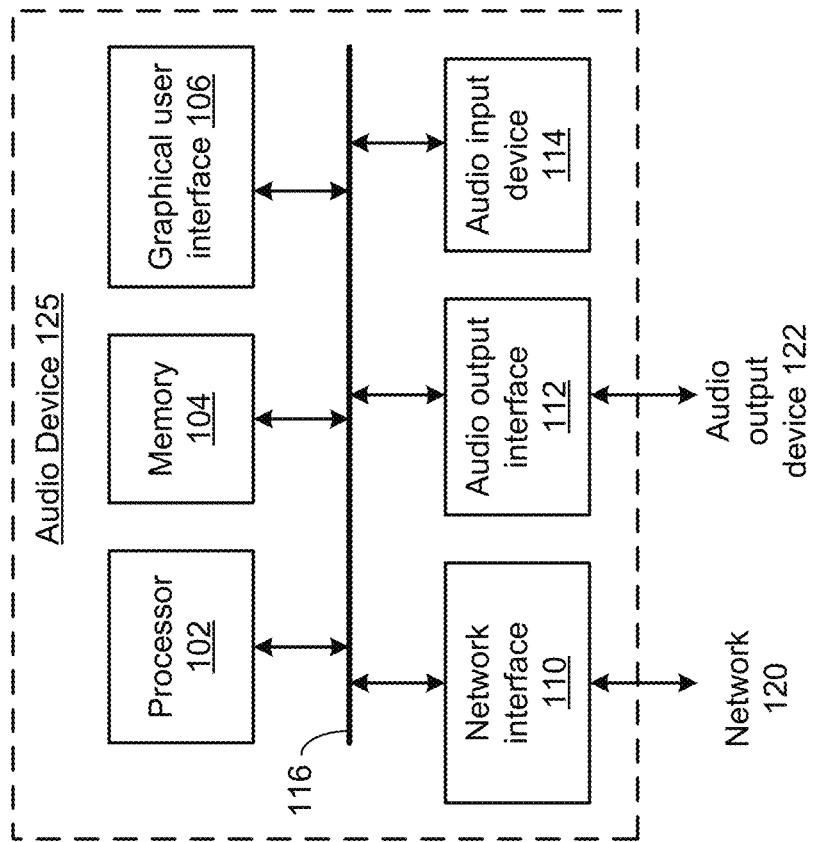
FIG. 1 presents a block diagram representation of an audio device in accordance with an embodiment of the present invention.

FIG. 1 presents a block diagram representation of an audio device in accordance with an embodiment of the present invention. In particular, an audio device 125 is presented that includes a processing system having at least one processor 102 and memory 104, a graphical user interface 106, a network 110, an audio output interface 112 and an audio input device 114 that are coupled via a bus 116. The audio device 125 can be a smart phone, netbook, notebook, tablet, personal computing device, portable game player, or other electronic device that is capable of playing audio files and/or displaying media content. While specific elements of audio device 125 are presented to facilitate the discussion herein, other elements (not specifically shown) can likewise be included.

Processor 102 controls the operation of the audio device 125 and/or provides processing required by other modules of the audio device 125. The processor 102 can each be implemented using a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in a memory, such as memory 104. Memory 104 can be a single memory device or a plurality of memory devices. Such a memory device can include a hard disk drive or other disk drive, read-only memory, random access memory, volatile memory, non-volatile memory, static memory, dynamic memory, flash memory, cache memory, and/or any device that stores digital information. Note that when the processor 102 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. While a particular bus structure is shown, other architectures, including the use of additional busses and/or direct connectivity between elements are likewise possible.

Network interface 110 can include a wired connection to a network 120 such as an Ethernet connection, Universal Serial Bus (USB) connection, an Institute of Electrical and Electronics Engineers (IEEE) 1394 (Firewire) connection, small computer serial interface (SCSI) connection, a composite video, component video, S-video, analog audio, video graphics array (VGA), digital visual interface (DVI) and/or high definition multimedia interface (HDMI) connection or other wired connection that operates in accordance with a wireless interface protocol. Network interface 110 can also include a wireless connection to a network 120 that operates in accordance with a wireless network protocol such as 802.11a,b,g,n,as,ad (referred to generically as 802.11x), Ultra Wideband (UWB), 3G, 4G, 5G voice and data protocol, Bluetooth, Zigbee, 802.11x, Infrared Data Association (IrDA) or other or other wireless protocol. The network 120 can be a personal area network, local area network, wide area network and/or the Internet.

The graphical user interface (GUI) 106 can include a display device such as a liquid crystal display, cathode ray tube, plasma display, light emitting diode display or any other display screen that creates an optical image stream either directly or indirectly, such as by optical transmission or projection, and/or that produces an audio output. The display device can include a resistive touch screen, capacitive touch screen or any other display screen that generates touch data in response to the touch of the display screen or near touch by a user, a stylus or other pointing object. The GUI 106 can also include one or more buttons or switches, soft keys, a touch pad, mouse, a remote control device, such as an infrared or other wireless and remote control interface that communicates with the remote control device, in addition to other devices and drivers that allow the user to interact with the audio device 125.

The audio input device 114 includes a microphone that responds to the voice of the user or other sounds to generate voice data that can be recorded as an audio file. The audio output interface 112 can include wired connection such as an analog stereo audio jack, a headphone jack, a digital audio jack, a wireless data connection such as a Bluetooth, Zigbee, 802.11x, Infrared Data Association (IrDA) or other interface that couples an audio signal to a separate audio output device 122, such as headphones, one or more speakers, stereo system, home theatre audio system or other audio output device.

In operation, the processor 102 loads and executes an auditory simulation application stored in memory 104. In particular, the auditory simulation application includes instructions that configure the processing system to perform various operations described herein. The processing system selects one of a plurality of audio files, stored in memory 104, in response to user interaction with the graphical user interface 106. The audio files can include music files downloaded to the audio device 125 from the network 120 via the network interface 110. The audio files can further include audio test files used in conjunction the testing of a user's hearing and/or sample audio files that can be used to demonstrate the response of the ear to various types of audio signals, various types of sounds and/or various frequencies. The audio files can also include recorded audio files generated by audio input device 114 and stored in memory 104 and/or audio files that are streamed from a remote device via the network interface 110. The audio files can be formatted in accordance with one or more audio file formats such as WAV, AIFF, AU, PCM, FLAC, Monkey's Audio, WavPack, TTA, ALAC, MPEG-4 SLS, MPEG-4 ALS, MPEG-4 DST, Windows Media Audio (WMA), Shorten (SHN), Opus, MP3, Vorbis, Musepack, AAC and/or ATRAC for playback by a standard Windows, Android or IoS audio player or other audio player utility or application.

The processing system decodes the selected audio file to generate audio output signals for playback of the selected audio file via an audio output device 122 or an audio output device included in the GUI 106. The processing system generates animated auditory system display data in response to the selected one of the plurality of audio files and for display via the display device. The animated auditory system display data, when displayed on the display device of the GUI 106, animates the action of one or more elements of a human ear or a pair of ears. In various embodiments, the processing system responds to user interaction with the graphical user interface to select the element or elements of the ear to be animated from a plurality of elements such as, a cochlea, an auditory nerve, an eardrum, and/or an ear bone (malleus, incus and/or stapes). For example, in response to user selection of the cochlea, the processing system animates the action of one or more simulated cochlea in response to the selected audio file. In various embodiments, the processing system is further configured by the auditory simulation application to respond to user interaction with the graphical user interface in order to modify a viewing perspective of the simulated cochlea or other element of the ear presented by the animated auditory system display data; allowing, for example, the user to select an angle in three-dimensions to view the simulated cochlea or other ear element. The processing system can further to respond to user interaction with the graphical user interface in order to modify a viewing magnification of the simulated cochlea or other ear element presented by the animated auditory system display data; allowing, for example, the user to zoom in and out of a selected point of the simulated cochlea or other ear element. In addition, different levels of zooming can add more details in addition to changing the magnification. For instance a high level of zooming on the cochlea could show the individual rows of hair cells.

In various embodiments, the processing system is further configured by the auditory simulation application to test the hearing of the user of the audio device 125. In this mode of operation, the processing system generates the audio output signals for playback of auditory test signals via an audio output device 122 or other audio output device such as headphones or a speaker included in GUI 106. The processing system responds to user interaction with the GUI 106 to receive auditory feedback indications from a user of the audio device 125 in response to the playback of the auditory test signals, for example, indicating which signals were heard by the user. The processing system analyzes the auditory feedback indications from the user to generate user profile data corresponding to the user that includes hearing test data that indicates hearing of the user. In further examples, a model of the user's hearing can be developed based on automatic calibration carried out by measurement of the otoemissions (with an in-ear microphone) and/or action potentials (such as via patch electrodes, electrodes built into headphones or other electrodes in contact with the head of the user in proximity to the ear or ears). Such testing can be also be used to generate hearing test results, other user profile data and/or compared against the expected model results from other hearing tests.

In various embodiments, the processing system is further configured by the auditory simulation application to receive or manually enter hearing test results of the user of the audio device 125. For example, the processing system can respond to user interaction with the graphical user interface to receive hearing test data from a user of the audio output device. The processing system generates, in response to the hearing test data, user profile data corresponding to the user that indicates hearing of the user.

In various embodiments, the processing system can optionally modify the animated auditory system display data based on the user profile data to indicate the hearing of the user, based on either hearing test data received by the audio device 125 or test results generated from testing performed by the audio device 125. In this fashion, the animated display of the simulated cochlea or other ear element can reflect the user's actual hearing, can be compared to ideal hearing, hearing of other users, etc.

In various embodiments, the processing system is further configured by the auditory simulation application to provide compensation for the hearing of the user of the audio device 125. The processing system generates hearing compensation parameters of the user, based on the user profile data corresponding to the user that indicates the hearing of the user. The processing system can then modify the animated auditory system display data based on the user profile data to indicate the hearing of the user and the hearing compensation parameters of the user and/or modify the audio output signals, according to the hearing compensation parameters of the user, for playback of the selected one of the plurality of audio files via the audio output device 122 or audio output device of the GUI 106.

In various embodiments, the processing system can optionally modify the animated auditory system display data based on the user profile data to indicate the predicted future hearing of the user. For example, the processing system responds to user interaction with the graphical user interface to select a future hearing model for a user of the audio output device and modifies the animated auditory system display data based on the future hearing model to indicate a prediction of future hearing of the user. In this fashion, the animated display of the simulated cochlea or other ear element can reflect predictions of hearing degradation over time, at particular ages, after a certain number of years, in response to certain lifestyle changes that may protect hearing or slow hearing loss, etc.

In various embodiments, simulating the action of the cochlea includes simulating excitation of cochlear nerves, other portions of the ear, and/or the brain of the user. The processing system generates the animated auditory system display data in response to the selected one of the plurality of audio files by: separating the audio output signals into a discrete number of frequency components each having a corresponding component frequency; extracting an amplitude of each frequency component and generating amplitude data based on the amplitude of each frequency component; generating a simulated waveform for each frequency component, based on the amplitude data and a simulated frequency that is different from the component frequency; and simulating the action of the cochlea for each frequency component at a position along the at least one simulated cochlea or other ear element corresponding to the corresponding component frequency for each frequency component, based on the simulated waveform for each frequency component. In particular, the simulated waveform for each frequency component can be further based on hearing test data or other user profile data of a user, hearing compensation data for a user and/or a prediction of future hearing of a user.

In various embodiments, the animated auditory system display data is generated in response to user interaction with the graphical user interface to select one of a plurality of cochlear images. This allows the simulated cochlea or other ear element to be displayed anatomically, with a simplified pseudo-anatomical representation, a non-anatomical representation or even as a whimsical, artistic or fanciful representation that may include merely a vague similarity to an actual cochlea.

The further operation of the audio device 125 can be described in conjunction with the following examples presented in conjunction with FIGS. 2-16 that follow.

FIG. 2 presents a block diagram of a memory in accordance with an embodiment of the present invention. In the embodiment shown, memory 104 includes an auditory simulation application 200, user profile data 202, auditory compensation data 204, hearing prediction data 206, audio files 208 and cochlear image data 210. While not specifically shown, the memory 104 includes a register space, buffer space, an operating system and systems utilities, other user data files and other applications of the audio device 125, such as a browser, standard audio player, phone and messaging apps, games, etc.

The auditory simulation application 200 includes operational instructions that, when executed by the processor 102, perform the functions of the audio device 125 described herein. The user profile data 202 can include information indicating the preferences and subscriber information pertaining to one or more users of the audio device 125.

In addition, the user profile data 202 includes hearing test data that is manually entered into, received by or generated by the audio device 125. In various embodiments, the hearing test data can be formatted as a set of n gains ($A_1$, $A_2$, ... $A_n$) for each ear corresponding to a plurality of n frequencies ($f_1$, $f_2$, ... $f_n$) in the range of audible hearing. Similarly, the auditory compensation data can be formatted as a set of n gains ($B_1$, $B_2$, ... $B_n$) for each ear corresponding to the n frequencies ($f_1$, $f_2$, ... $f_n$) in the range of audible hearing. Furthermore, the hearing prediction data 206 can be formatted as a set of n gains ($C_1$, $C_2$, ... $C_n$) for each ear corresponding to the n frequencies ($f_1$, $f_2$, ... $f_n$) in the range of audible hearing, for each of a plurality of ages and further for each of a plurality of differing prediction models such as a high hearing care model, an average model and a low hearing care model. It should be noted that any of the frequencies above can span a full range of audible hearing such as 20 Hz to 20 KHz or a selected or variable narrower range of frequencies within this range. In particular, while the range of 20 Hz to 20 KHz is often mentioned, very few adults actually have that full range and the model can be further customized. In addition, other model customization can be employed. The auditory simulation application 200 can also include an option to enter any suspected hair cell damage for each frequency range. The model in this case can include nonlinear effects, for example, that go beyond mere differences in amplitude.

The audio files 208 can include files with auditory test signals, example signals, recorded audio, music, and/or other audio files in one or more audio file formats. The cochlear image data includes data for simulating the cochlea in a plurality of selectable image formats including, for example, data for displaying cochlea anatomically, pseudo-anatomically and/or non-anatomically.

FIG. 3A presents a block diagram representation of an auditory simulation application in accordance with an embodiment of the present invention. In the embodiment shown, the auditory simulation application 200 includes a simulation module 302, a test module 304, a prediction module 306, a compensation module 308 and a playback module 310.

The simulation module 302 provides instruction to the processing system to select one of a plurality of cochlear images included in cochlear image data 210 based on user input and further to simulate the action of cochlea in response to a selected audio file 208 and to generate animated auditory system display data for display via the display device of the audio device 125. The simulation module 302 also allows the processing system to respond to user interaction with the graphical user interface 106 in order to modify a viewing perspective of the simulated cochlea or other ear element and/or to modify a viewing magnification of the simulated cochlea or other ear element presented by the animated auditory system display data; allowing, for example, the user to switch viewing angles, zoom in and out of a selected point of the simulated cochlea or other ear element, etc. As previously discussed, the simulation module 302 can provide instructions to the processing system to not only simulate the action of the cochlea, but also the excitation of cochlear nerves and/or other operations of the ear. Further, the simulation of the cochlea can be based on hearing test data included in user profile 202, auditory compensation data 204, and hearing prediction data 206 for any one of the audio files 208 selected by the user via GUI 106.

The test module 304 provides instructions to the processing system to selectively test the hearing of each ear the user of the audio device 125 and to generate hearing test data that indicates hearing of the user and/or to receive or manually enter hearing test data from separate hearing test results of the user of the audio device 125. The test module stores either form of hearing test data as part of the user profile data 202.

The compensation module 308 provides instructions to the processing system to provide compensation for the hearing of the user of the audio device 125. The processing system generates hearing compensation parameters of the user for storage as auditory compensation data 204. As discussed in conjunction with FIG. 2, hearing test data can be formatted as a set of n gains $(A_1, A_2, \ldots A_n)$ for each ear corresponding to a plurality of n frequencies $(f_1, f_2, \ldots f_n)$ in the range of audible hearing. Considering an ideal and normalized response where $A_i=1$, for $i=1,2 \ldots n$ A user's actual hearing can be attenuated in one or more of these frequency ranges due to hearing loss, resulting in a corresponding gain at that frequency that is less than 1. The auditory compensation data can be represented as a set of n gains $(B_1, B_2, \ldots B_n)$ for each ear, to equalize the hearing test data for each frequency such that:

$A_i B_i=1$, for $i=1,2 \ldots n$

Or $B_i=1/A_i$, for $i=1,2 \ldots n$

It should be noted that while the discussion of compensation above has focused on full compensation, a partial compensation can be employed. In various embodiments, the auditory simulation application can modify the hearing compensation parameters of the user based on user interaction with the graphical user interface to select a level of partial compensation for hearing of the user. In some cases a full compensation with high gain (>30 dB) may lead to user discomfort, and a partial compensation of 20-30 dB may be more suitable. In addition to hearing the results of the compensation on the audio output, users can visualize the partial compensation via the animation to select the amount of compensation to apply, either as a portion of total compensation or on a frequency by frequency basis. It should also be noted that the maximum compensation can be limited to a single fixed value or as a series of fixed values for each frequency.

Furthermore, while particular compensation methodologies are discussed above, other techniques such as FIR filters, banks of bi-quad IIR filters, or other filtration, compensation or equalization can likewise be employed. In addition, the hearing test data can generated for a particular listening environment including a place (such as an automobile, bicycle, motorcycle, boat or other vehicle, a room, etc.), the location of the user in the place and the particular audio equipment that is to be used. The hearing compensation parameters of the user can not only provide compensation for the user's hearing, but also further provide equalization for the particular listening environment. In this fashion, the auditory simulation application can provide compensation for hearing loss and the particular environment to create a fully calibrated sound experience.

The prediction module 306 provides instructions to the processing system to indicate the predicted future hearing of the user. For example, the processing system responds to user interaction with the graphical user interface to select a future hearing model and a corresponding set of hearing prediction data 206 for a user of the audio output device. Considering again the hearing test data can be formatted as a set of n gains $(A_1, A_2, \ldots A_n)$ for each ear and the hearing prediction data 206 of the selected future hearing model to be the set of n gains $(C_1, C_2, \ldots C_n)$ for each ear, that provide further attenuation at one of more frequencies. The total attenuation for the ith frequency can be represented by the product $A_i C_i$. The hearing prediction data can be generated based on the age of the user at a future date based on expected hearing loss data for that age. In addition, the amount of current hearing loss can be extrapolated to automatically estimate a future loss. For example if a 20 year-old person currently has the hearing of a 45-year-old, this accelerated loss can be extrapolated forward in time to generate more accurate predictions of additional future hearing loss for this person.

While the foregoing has focused on predicting future hearing of the user, the auditory simulation application can otherwise respond to user interaction with the graphical user interface to select a level of hearing impairment for himself, herself or another user. The animated auditory system display data and/or audio output based on the selected level of hearing impairment. In this mode of operation, a user with good hearing can hear what damaged hearing sounds like in addition to visualizing the changes in hearing on the ear. This can be particularly useful for a person with relatively good hearing to experience the hearing of others, for example, to help an aging parent make a decision regarding hearing aids.

The playback module 310 can include an audio player, such as a standard Windows, Android or IoS audio player or other audio player utility or application with a programmable equalizer that generates an audio output signal from the selected audio file. The auditory compensation data $(B_1, B_2, \ldots B_n)$, can be applied to equalize the hearing test data for each frequency and each ear of the user to compensate for potential hearing loss at each frequency. Further, while the foregoing examples have focused on playback of stored audio files, in other embodiments, the playback module of audio device 125 can furthermore apply auditory compensation data to generate compensated audio in response to streaming audio content, broadcast audio content and/or other audio data. In addition or in the alternative, the equalization can apply the hearing prediction data 206 $(C_1, C_2, \ldots C_n)$ for each ear to demonstrate to the user the possible effects of hearing loss at some future time or some future age of the user. In this fashion, the user can listen to the effects of possible hearing loss in (5, 10, 15, 20 . . . ) years' time or at a particular age (45, 50, 55, 60 . . . ) based on different models of hearing care selectable by the user.

FIG. 3B presents a graphical diagram 350 representation of an audio signal in accordance with an embodiment of the present invention. A portion of an audio signal is shown as a function of time that represents a music file that can be used to illustrate an embodiment of how the simulation module 302 operates to generate the animated auditory system display data. The processing system identifies sample windows in the signal characterized by periods of high signal energy. In the example shown, four sample windows T1, T2, T3 and T4 are identified. The audio signal from each sample window is processed by the processing system by first separating the audio signal into a discrete number of n frequency components corresponding to the n frequencies ($f_1, f_2, \ldots f_n$). This separation can be performed via a Fast Fourier Transform or other discrete Fourier transform, via bandpass filtration and envelope detection or via other signal processing.

An amplitude corresponding to each frequency component is extracted and amplitude data is generated as a function of time ($x_1(t), x_2(t), \ldots x_n(t)$) for each frequency component and each ear. For the purposes of simulation, values of the amplitude data can be compared to a threshold and set to zero if lower than the threshold to yield processed amplitude data ($x'_1(t), x'_2(t), \ldots x'_n(t)$). A simulated waveform is generated for each frequency component, based on the amplitude data and a simulated frequency that is different from the component frequency. In particular, the standard audible frequency range of 20 Hz to 20 KHz include many frequencies of cochlear excitation that are too fast to discern by the human eye. The n frequency components corresponding to the n frequencies ($f_1, f_2, \ldots f_n$) can be converted to a compressed set of corresponding simulated frequencies ($f'_1, f'_2, \ldots f'_n$), in the range of 3-10 Hz that can be more easily discerned by the human eye. The simulated waveform $w_i(t)$ for the ith frequency component i can be represented by:

$$w_i(t)=cx'_i(t)\cos(2\pi f'_i t)$$

where c is a scaling constant. While a frequency synthesis approach is presented above, the simulated waveform can be generated in other fashions, such as via frequency down conversion to the simulated frequency or via other frequency conversion process that, for example, preserves a monotonically increasing relationship between frequencies while lowering the frequencies for greater visualization and also compressing the range of frequencies. As previously discussed, the simulated waveform for each frequency component can be based further on hearing test data included in user profile data 202, auditory compensation data 204, and/or hearing prediction data 206. Taking into consideration the hearing test data for the user:

$$w_i(t)=A_i cx'_i(t)\cos(2\pi f'_i t)$$

Taking into consideration the hearing test data for the user and hearing prediction data data:

$$w_i(t)=A_i B_i cx'_i(t)\cos(2\pi f'_i t)$$

Taking into consideration the hearing test data for the user and auditory compensation data:

$$w_i(t)=A_i C_i cx'_i(t)\cos(2\pi f'_i t)$$

The action of the cochlea can be simulated for the ith frequency component at a position along the at least one simulated cochlea or corresponding to the corresponding component frequency $f_i$ by applying oscillatory motion at this position of the form $w_i(t)$.

While the forgoing has described the simulation process for a single sample window, the process can be repeated for each sample window in the audio signal. In an embodiment, times between sample windows can represented without cochlear excitation. In a further embodiment, however, the waveforms for each sample window are expanded to a series of expanded sample windows T'1, T'2 . . . that are synchronized with the position of the original sample windows but that fill some or all of the gaps in the audio signal between sample windows. In this case, the processed amplitude data can be stretched in time to fill each expanded sample window as:

$$w_i(t)=cx'_i(\alpha+t/\beta)\cos(2\pi f'_i t)$$

where the values of $\alpha$ and $\beta$ are selected to correspond to the amount of expansion and the time synchronization of the simulated waveform with the audio signal. Hearing test data $A_i$, auditory compensation data $B_i$, and/or hearing prediction data $C_i$ can also be included as discussed above.

While a particular simulation process is described above, other techniques can be used as well. For example, samples of the audio signal can be taken at short time intervals, (5 msec every 1 sec, for example). The simulation can be generated by waveforms that are 200 times slower. In addition to that, the particular 5 ms interval to use can be chosen based on an envelope detector which picks the highest signal during that time. The advantage of this mode of operation is that it's anatomically and timing accurate.

It should be noted the forgoing examples are merely illustrative of the many different ways that cochlear excitation can be simulated and animated.

Figure 4:
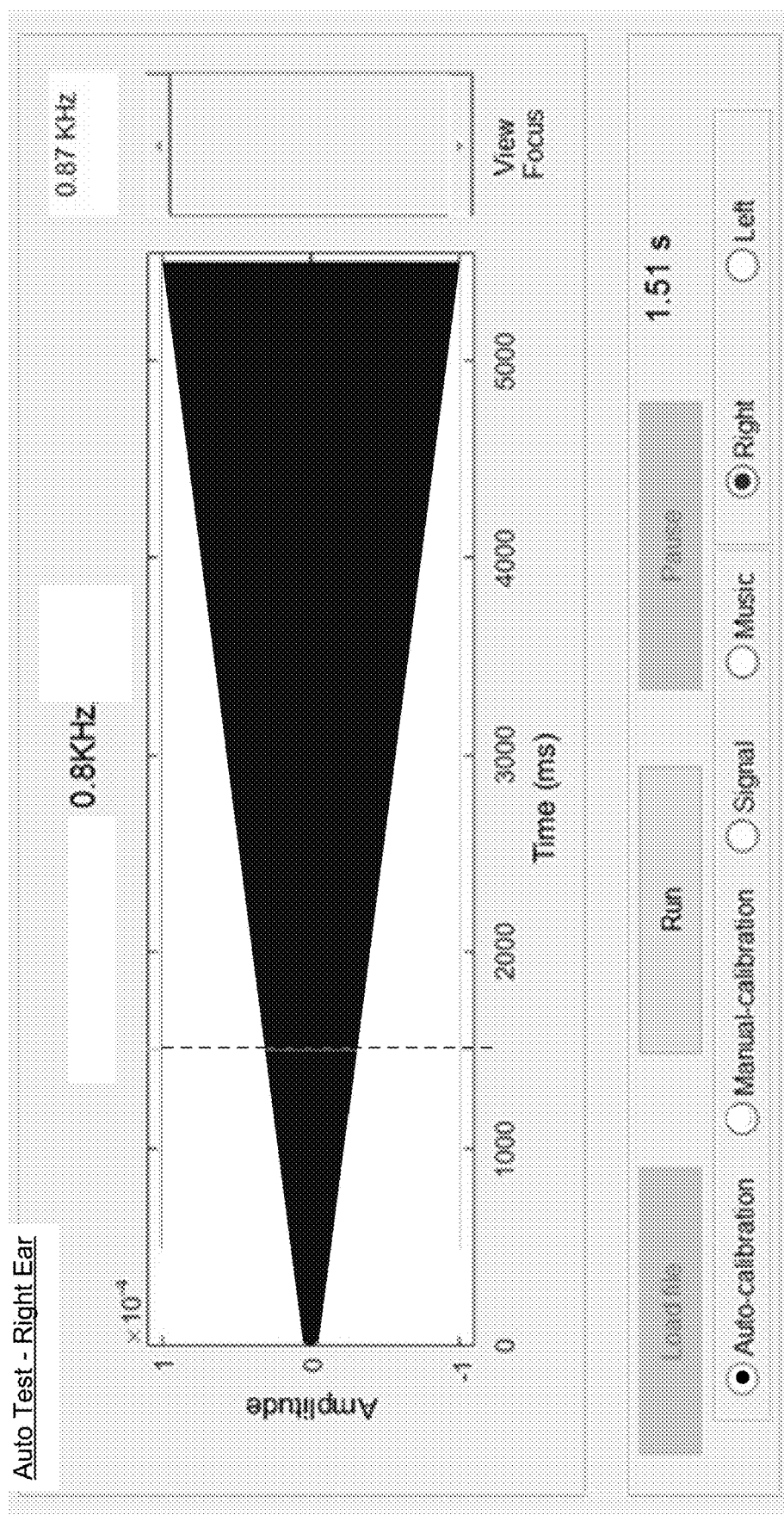
FIG. 4 presents a pictorial representation of a screen display in accordance with an embodiment of the present invention.

FIG. 4 presents a pictorial representation of a screen display in accordance with an embodiment of the present invention. As previously discussed, the processing system can be configured by the auditory simulation application to test the hearing of the user of the audio device 125. In this mode of operation, the processing system generates the audio output signals for playback of auditory test signals via an audio output device 122 or other audio output device such as headphones or a speaker included in GUI 106. The processing system responds to user interaction with the GUI 106 to receive auditory feedback indications from a user of the audio device 125 in response to the playback of the auditory test signals, for example, indicating which signals were heard by the user. The processing system analyzes the auditory feedback indications from the user to generate user profile data corresponding to the user that includes hearing test data that indicates hearing of the user.

The screen display 400 represents the display of the GUI 106 during such a test. In the example shown, a 0.8 KHz tone with increasing amplitude is played into the right ear of the user. It should be noted that other combinations of signals or tones can be used, with either increasing or decreasing amplitude in order to ascertain the limit of the user's hearing for each frequency. For example, a simple tone, which sounds dry and almost irritating, can be replaced by a modulated signal around that tone, which can be rich and much more pleasing to the ear. The processing system responds to user interaction with the GUI 106 to receive auditory feedback indications from a user indicating at what time the signal was first heard by the user. The amplitude of the signal at the time the signal was first heard is saved and compared with an ideal hearing model for this user and playback of the tone is discontinued. Deviations from the ideal hearing model can be used to determine ($A_1, A_2, \ldots A_n$) for each ear. If for example, the user first heard a signal level that is 3 db above the ideal hearing sensitivity for that frequency, a −3 db can be stored as the user's hearing loss at this frequency as part of the user profile data 202.

Figure 5:
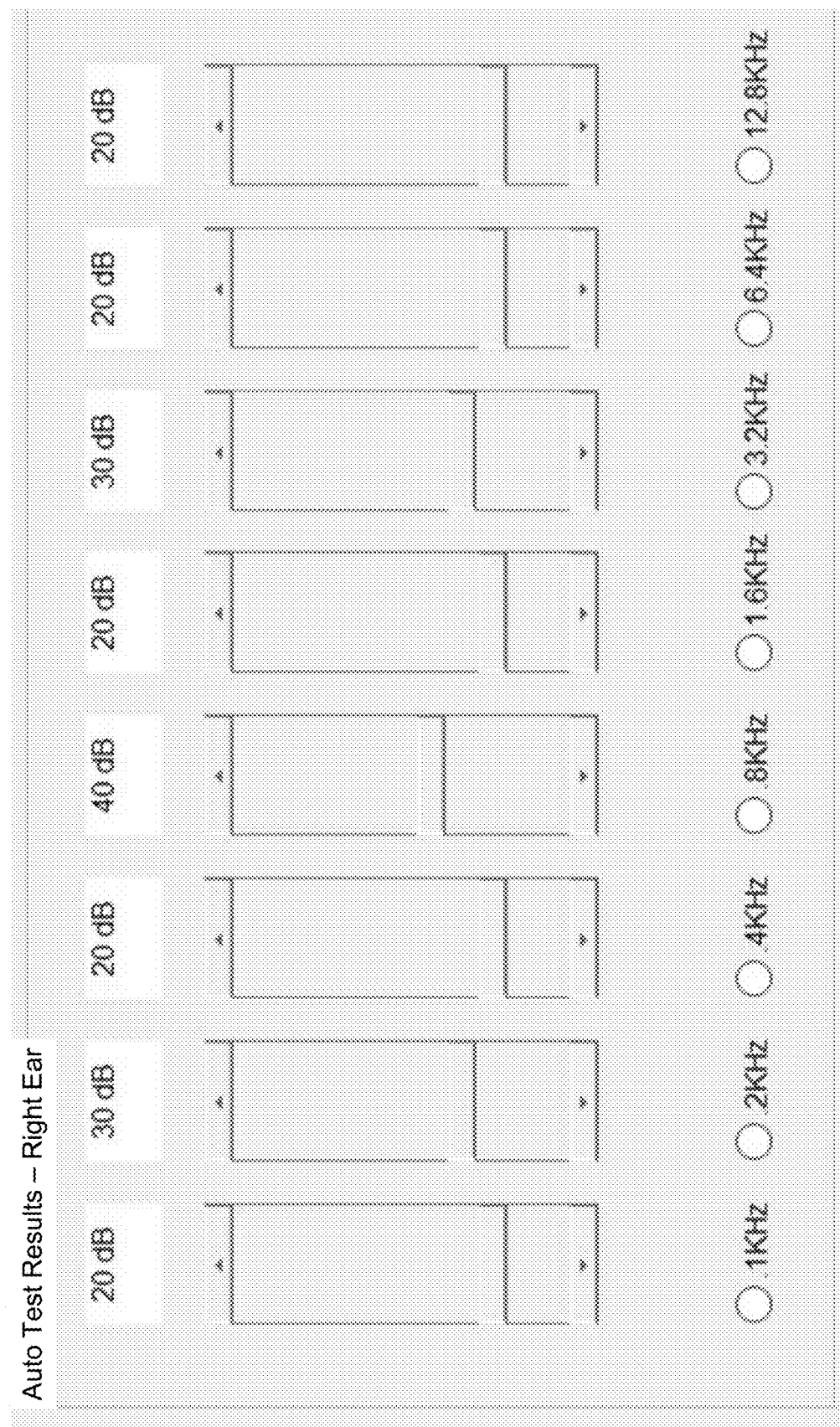
FIG. 5 presents a pictorial representation of a screen display in accordance with an embodiment of the present invention.

FIG. 5 presents a pictorial representation of a screen display in accordance with an embodiment of the present invention. The screen display 500 represents the display of the GUI 106 that indicates the results of an automatic hearing test of the right ear of a user. In particular, the user's hearing was tested over seven octaves from 100 Hz, to 12.8 KHz. In the example shown, the results are normalized to an ideal hearing sensitivity of 20 db which the user achieved for frequencies of 100 Hz, 400 Hz, 1.6 KHz, 6.4 KHz and 12.8 KHz. At other test frequencies however, the user's test results indicated decreased sensitivity with losses of 10 db at 200 Hz and 3.2 KHz and a loss of 20 db at 800 Hz.

Figure 6:
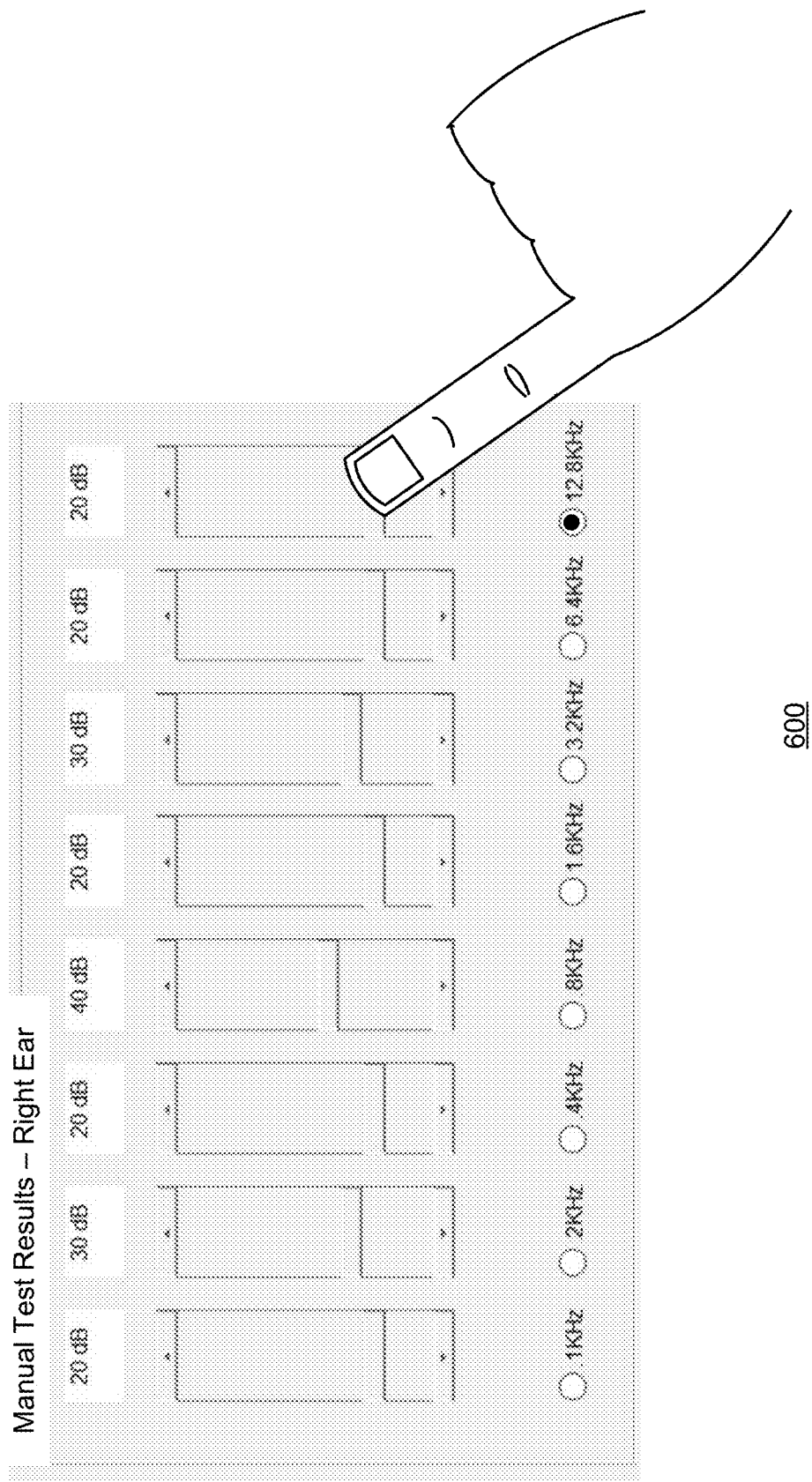
FIG. 6 presents a pictorial representation of a screen display in accordance with an embodiment of the present invention.

FIG. 6 presents a pictorial representation of a screen display in accordance with an embodiment of the present invention. The screen display 600 represents the display of the GUI 106 where the user manually enters test hearing test results. In this fashion, a user that has a professional hearing test can enter the results into the device by selecting a frequency and sliding the scale to correspond to the proper value.

As in the previous example, the user's hearing was tested over seven octaves from 100 Hz, to 12.8 KHz and the results were normalized to an ideal hearing sensitivity of 40 db which the user achieved for a frequency of 800 Hz. At other test frequencies however, the user's test results indicated decreased sensitivity with losses of 10 db at 200 Hz and 3.2 KHz and losses of 20 db at 100 Hz, 400 Hz, 1.6 KHz, 6.4 KHz and 12.8 KHz. In the example shown, the user has currently selected the 12.8 KHz frequency and has interacted with a touch screen implementation of GUI 106 to slide the scale to a position of 20 db.

Figure 7:
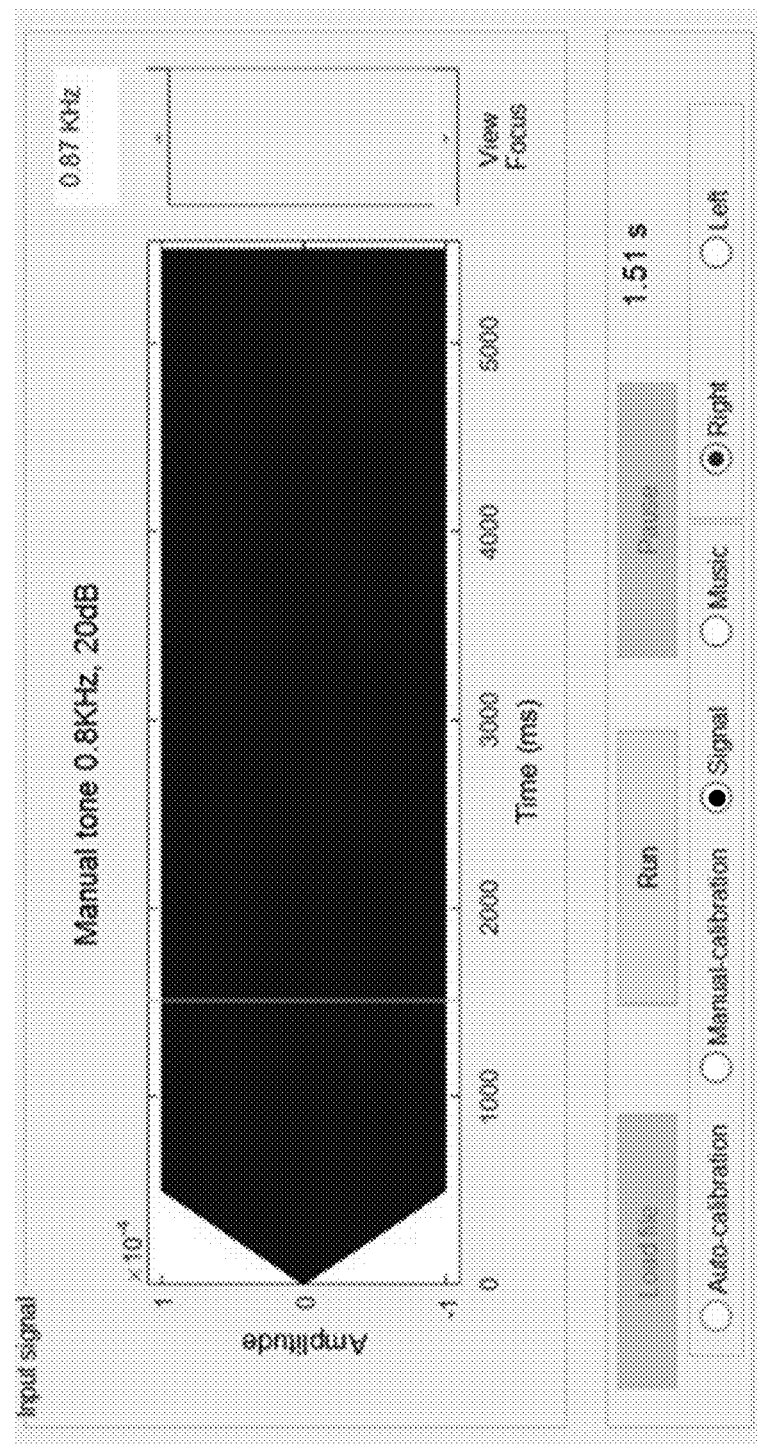
FIG. 7 presents a pictorial representation of a screen display in accordance with an embodiment of the present invention.

FIG. 7 presents a pictorial representation of a screen display in accordance with an embodiment of the present invention. In particular, a screen display 700 of GUI 106 is presented where the user has manually selected an audio file consisting of a 0.8 KHz 20 db tone for simulation and/or for playback. The GUI, 106 allows the user to select, load, run and pause the audio file. Progress in the file (currently 1.51 seconds) is indicated.

Figure 8:
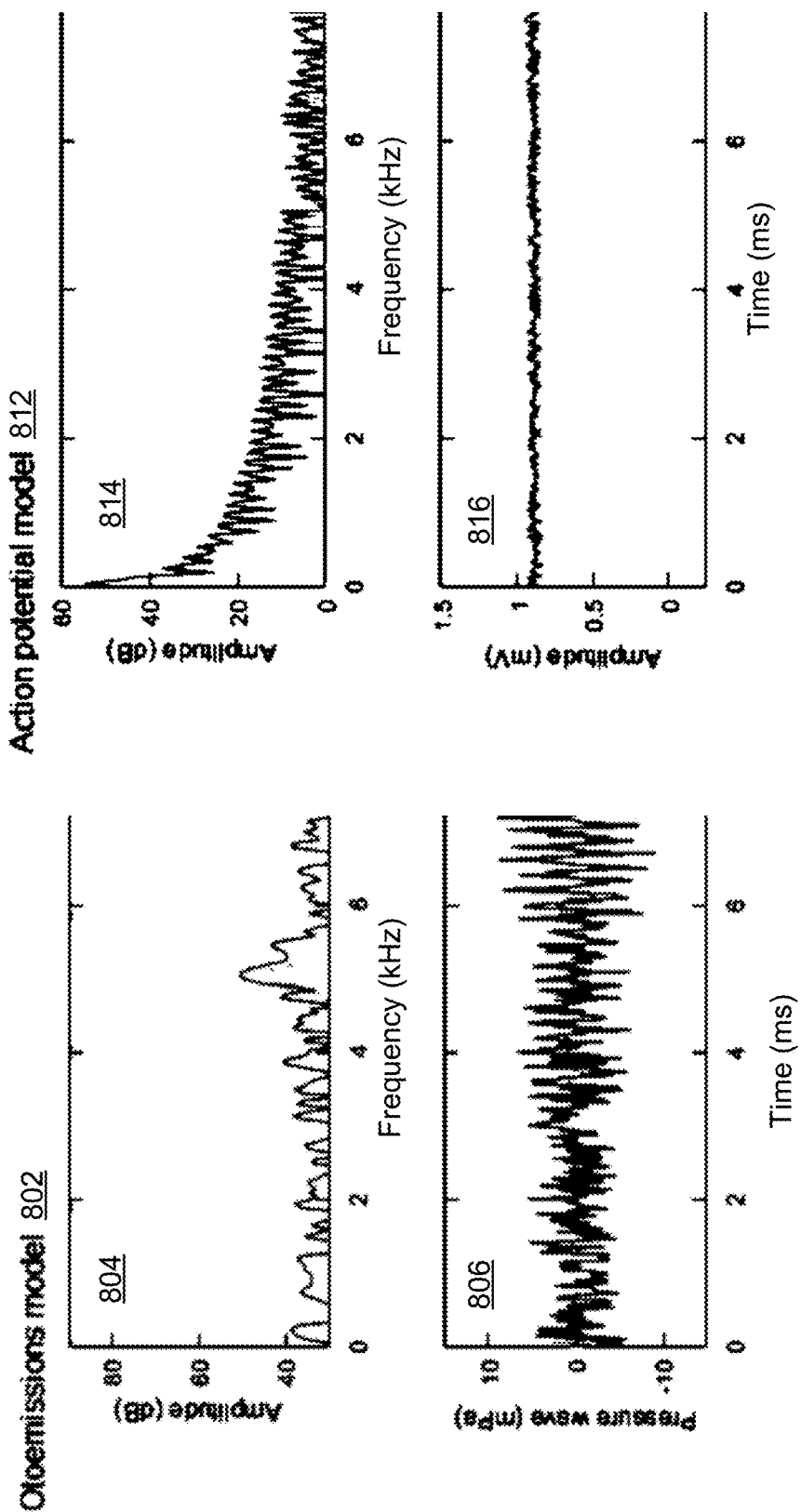
FIG. 8 presents graphical representations in accordance with an embodiment of the present invention.

FIG. 8 presents graphical representations in accordance with an embodiment of the present invention. While the forgoing has discussed animated cochlear simulations, the processing system of the audio device 125 can also present graphical outputs. In particular, a screen display 800 of GUI 106 is presented of an otoemissions model 802 of the ear that presents graphical outputs 804 and 806 in both the frequency and time domains. In addition, an action potential model 812 is presented that includes graphical outputs 814 and 816 in both the frequency and time domains.

Figure 9:
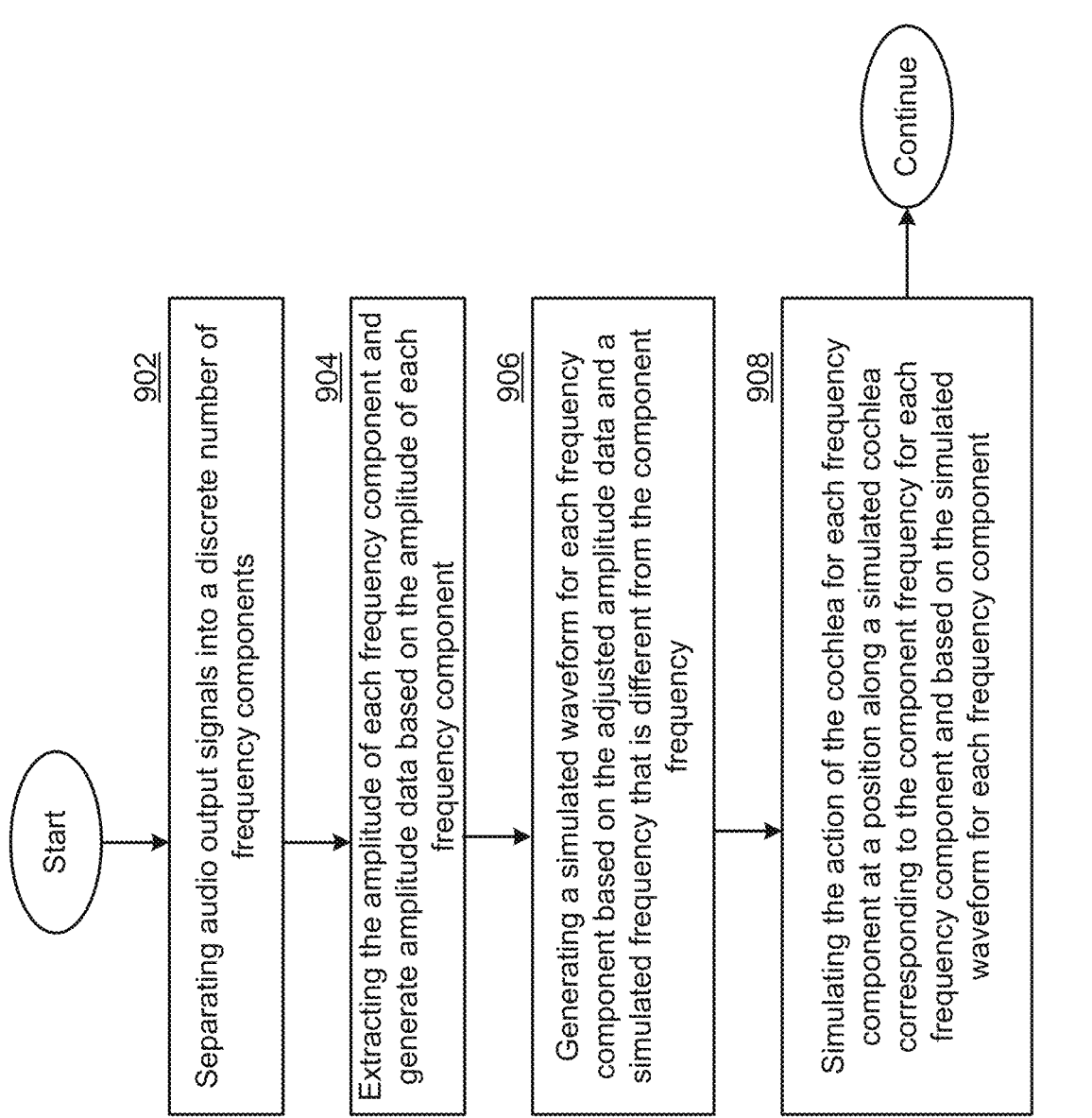
FIG. 9 presents a flow diagram representation of a method in accordance with an embodiment of the present invention.

FIG. 9 presents a flow diagram representation 900 of a method in accordance with an embodiment of the present invention. In particular, a method is presented for use in conjunction with one or more functions and features presented in conjunction with FIGS. 1-8.

Step 902 includes separating audio output signals into a discrete number of frequency components each having a corresponding component frequency. Step 904 includes extracting an amplitude of each frequency component and generating amplitude data based on the amplitude of each frequency component. Step 906 includes generating a simulated waveform for each frequency component, based on the amplitude data and a simulated frequency that is different from the component frequency. Step 908 includes simulating the action of the cochlea or other ear element for each frequency component at a position along the at least one simulated cochlea or other ear element corresponding to the corresponding component frequency for each frequency component, based on the simulated waveform for each frequency component.

In various embodiments, generating the simulated waveform for each frequency component can be further based on hearing test data from a user, hearing compensation data for the user and/or a prediction of future hearing of the user.

Figure 10:
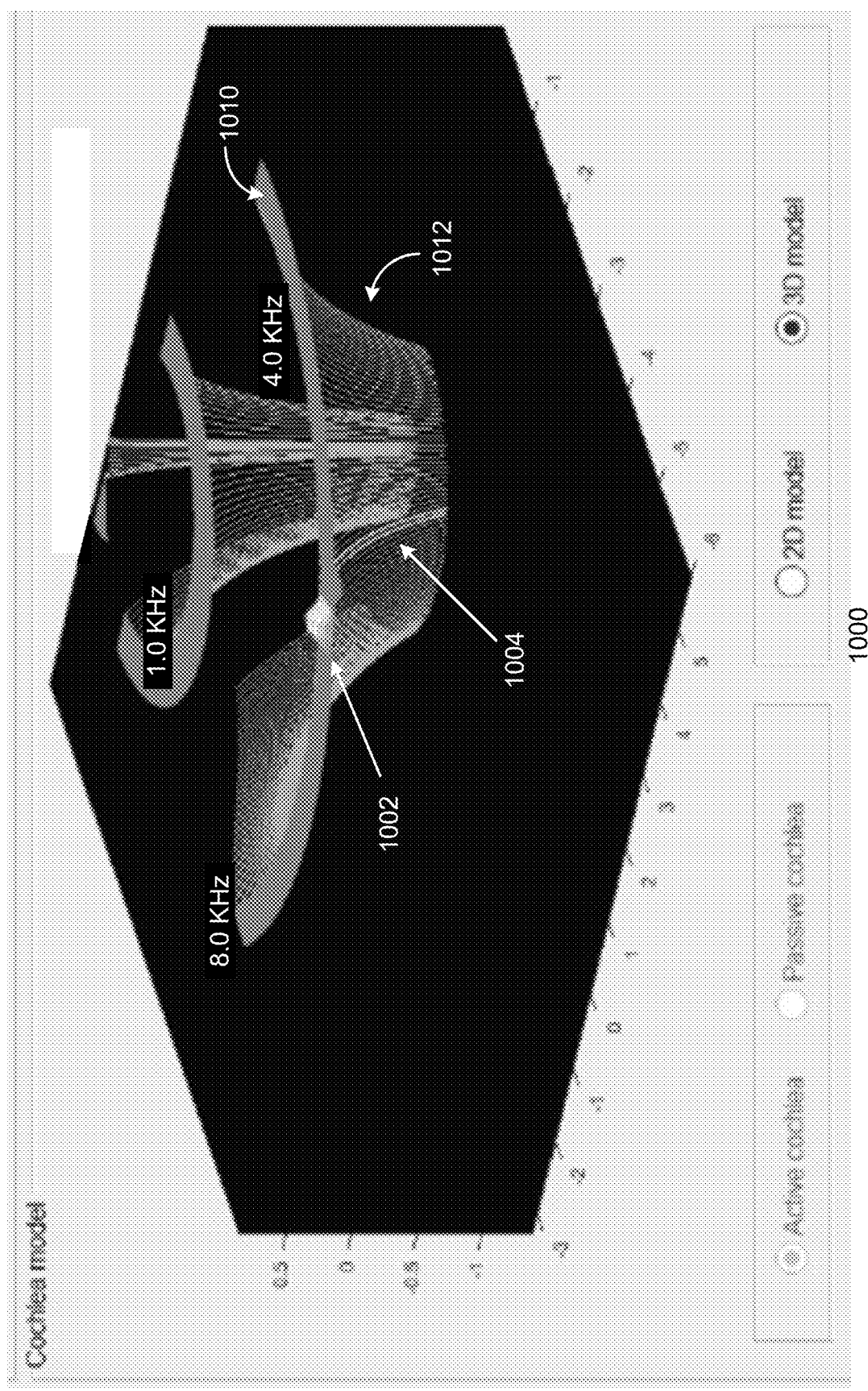
FIG. 10 presents a pictorial representation of a screen display in accordance with an embodiment of the present invention.

FIG. 10 presents a pictorial representation of a screen display 1000 in accordance with an embodiment of the present invention. In particular, a snapshot in time of an animated cochlear simulation is presented as displayed on a display device of the GUI 106 of audio device 125. In this case a three-dimensional pseudo-anatomical model of a single cochlea 1010 is presented along with cochlear nerves 1012 in response to a 6.4 KHz tone. The user has interacted with the GUI 106 to choose a viewing angle and magnification that presents the 6.4 KHz portion 1002 of the cochlea in front. The excitation of the cochlea in this region is indicated by the sinusoidal perturbation generated, for example, by the simulation waveform $w_i(t)$.

When viewing the animation, the user would see oscillatory motion of the 6.4 KHz portion 1002 of the cochlea at a simulation frequency, such as 7 Hz for example. In addition or in the alternative, excited regions of the cochlear and corresponding firing of the cochlear nerves 1004 can be indicated by changes in grayscale as shown or by changes in color. While an animated image of a cochlea of a single ear is presented, in various embodiments, the animated image can include the action of other portions of the ear, two ears with corresponding cochlea and/or neuron firings in the brain.

Figure 11:
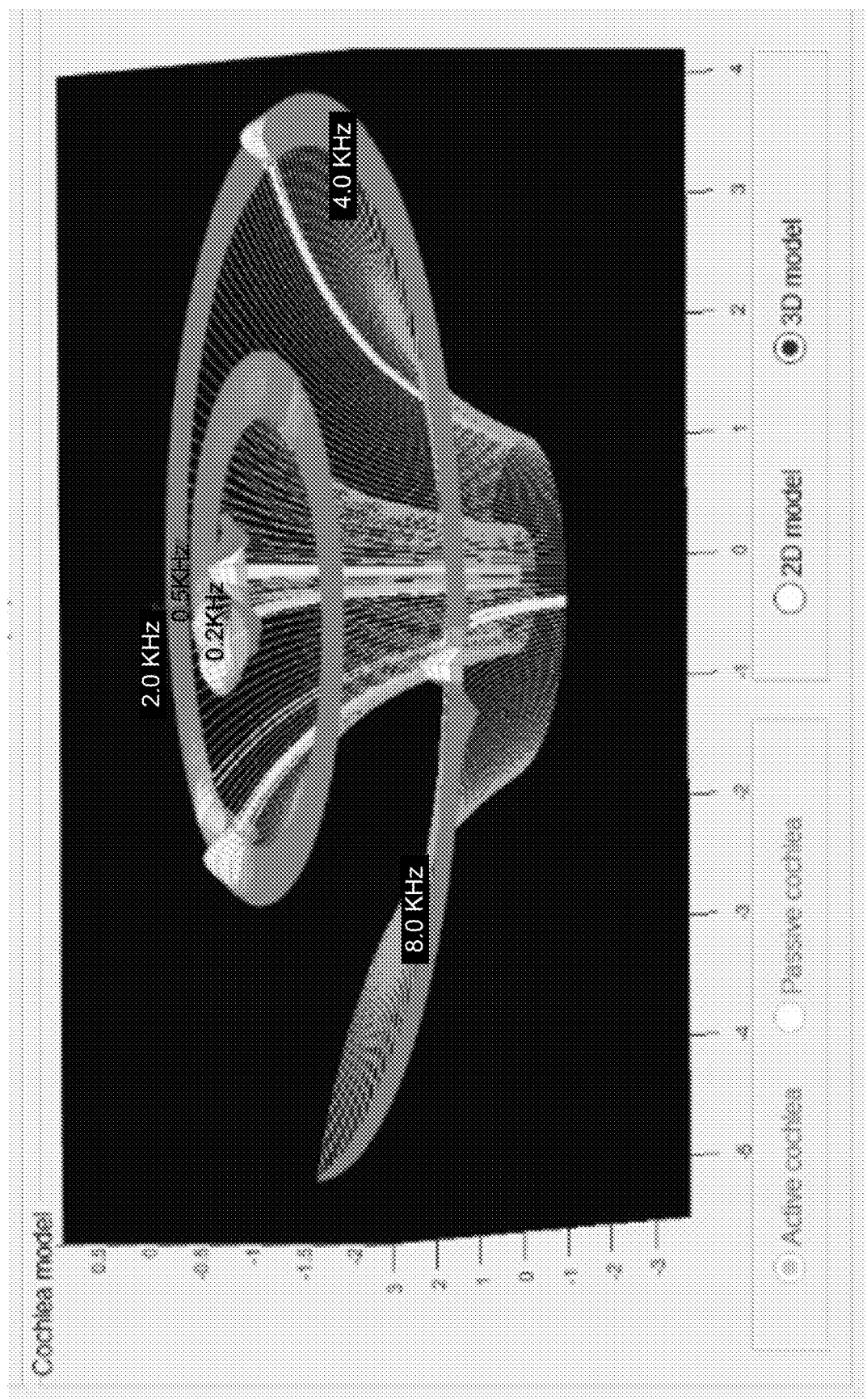
FIG. 11 presents a pictorial representation of a screen display in accordance with an embodiment of the present invention.

FIG. 11 presents a pictorial representation of a screen display 1100 in accordance with an embodiment of the present invention. In particular, a snapshot in time of an animated cochlear simulation is presented as displayed on a display device of the GUI 106 of audio device 125. In this case a three-dimensional pseudo-anatomical model of a single cochlea is presented along with cochlear nerves in response to a signal that includes a 100 Hz tone, 200 Hz tone, 400 Hz tone, 800 Hz tone, 1.6 KHz tone, 3.2 KHz tone and a 6.4 KHz tone. The user has interacted with the GUI 106 to choose a viewing angle and magnification that presents the 6.4 KHz portion of the cochlea in front. The excitation of the cochlea in is indicated by the sinusoidal perturbations generated, for example, by the simulation waveforms $w_i(t)$ at each frequency.

Figure 12:
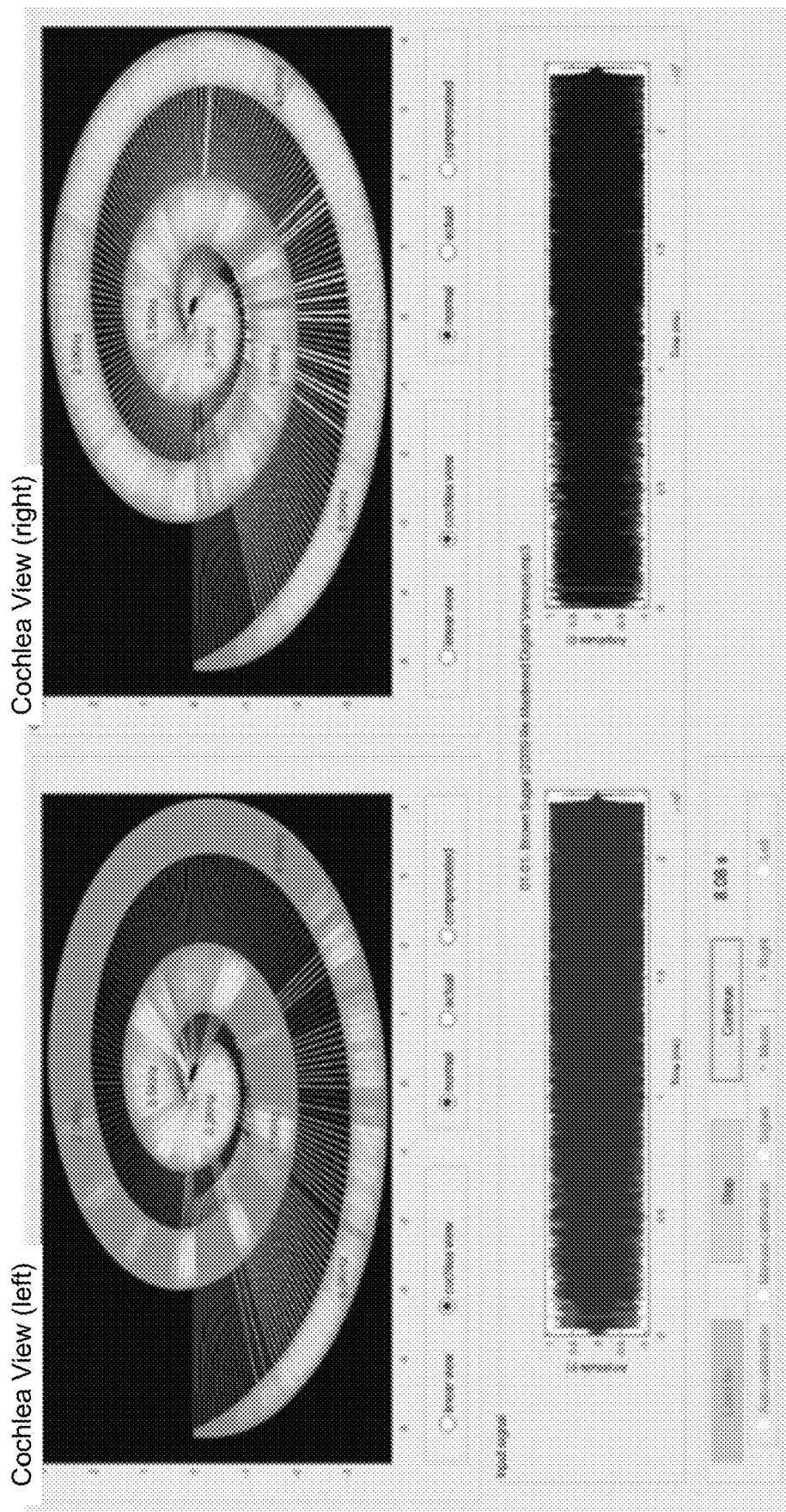
FIG. 12 presents a pictorial representation of a screen display in accordance with an embodiment of the present invention.

FIG. 12 presents a pictorial representation of a screen display 1200 in accordance with an embodiment of the present invention. In particular, a snapshot in time of an animated cochlear simulation is presented as displayed on a display device of the GUI 106 of audio device 125. In this case, three-dimensional pseudo-anatomical models of two cochlea (right and left) are presented along with cochlear nerves in response to playback of an audio file containing the song, Brown Sugar. The user has interacted with the GUI 106 to choose a viewing angle and magnification that presents a top view of each cochlea. The excitation of the cochlea in is indicated by the sinusoidal perturbations and color variations generated, for example, by the simulation waveforms $w_i(t)$ at much higher number of discrete frequencies. The firing of the cochlear nerves are also indicated by corresponding color variations. In this example, hearing test data for the user has been included in the simulation. The particular, this user has experienced hearing loss in the left ear and the simulation shows decreased cochlear excitation at some frequencies that is apparent in the differences between the animated simulations for the left and right ears.

Figure 13:
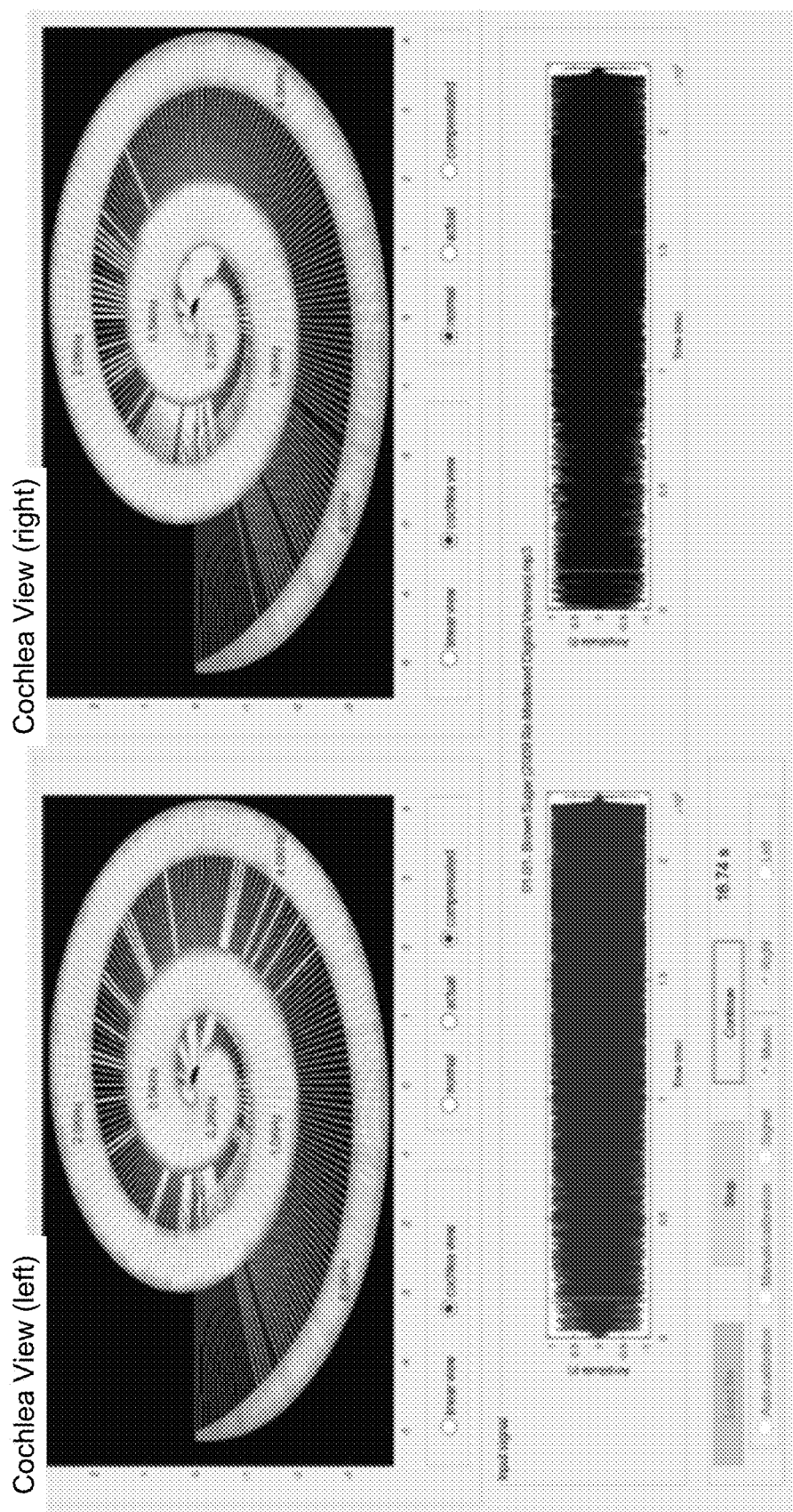
FIG. 13 presents a pictorial representation of a screen display in accordance with an embodiment of the present invention.

FIG. 13 presents a pictorial representation of a screen display 1300 in accordance with an embodiment of the present invention. In particular, a further example that follows along with the example presented in conjunction with FIG. 12. In this example, auditory compensation data has been applied to compensate for the user's hearing loss in the left ear. As shown in this example, the animated excitation of the simulated cochlea in the right and left ears track one another more closely.

The addition to merely modifying the simulation, the auditory compensation data can also be applied to the audio output of the audio device 125. By applying equalization to the output signal to the left speaker, earbud, etc. the user can experience an enriched audio playback that compensates for the user's hearing loss in the left ear.

FIG. 14 presents a pictorial representation of cochlear images in accordance with an embodiment of the present invention. While FIGS. 10-13 have presented animated cochlear simulations based on a pseudo-anatomical cochlear image, the user can select other cochlear images. Image 1400 is an example of an anatomical cochlear image. Image 1450 is an example of a fanciful, non-anatomical cochlear image with a spiral shape. These images merely provide examples of the wide range of cochlear images that can be employed in an animated cochlear simulation. For example, a "futuristic" image can be employed, or an image may be match to musical genre, the musical artist or the particular content of the audio filed being played. In other examples, the user can select a model image that matches the user's interest or taste such as a steampunk model, impressionist model, a gothic model, an architectural model, a musical model, a Disney character model, a Star Wars model, a Middle Earth model, a model of a place such as Niagara Falls, the Eiffel Tower, etc.

Figure 15:
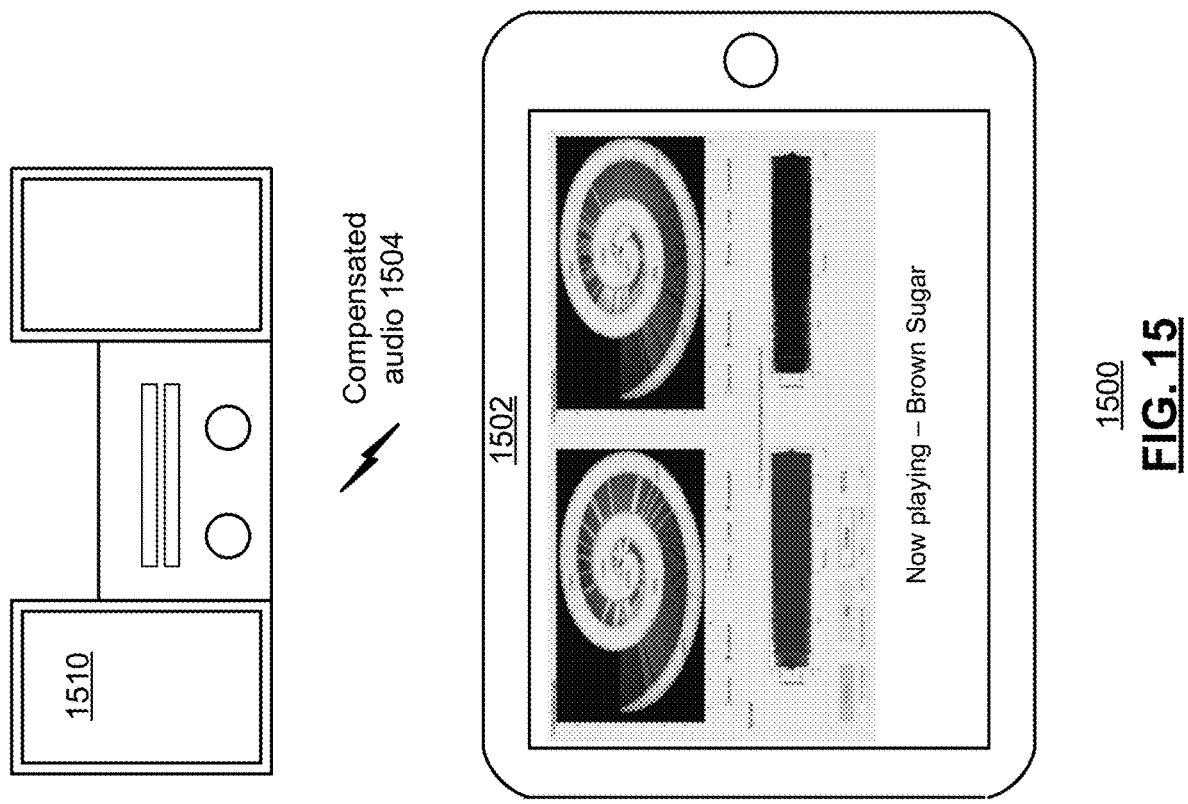
FIG. 15 presents a pictorial representation of an audio device and audio system in accordance with an embodiment of the present invention.

FIG. 15 presents a pictorial representation 1500 of an audio device and audio system in accordance with an embodiment of the present invention. In particular, the audio system includes a tablet 1502 that implements the audio device 125 that sends compensated audio 1504 via Bluetooth or other wireless connection to a home audio system 1510 such as a home stereo, home theatre system or Bluetooth speaker. Not only can the user select audio files for playback and view animated cochlear simulations on the tablet 1502, the auditory simulation application applies the auditory compensation data to the audio output sent as compensation audio 1504 that provides hearing loss correction. In this fashion, the user of tablet 1502 can enjoy audio playback of a selected music file that compensates for the user's hearing loss.

As previously discussed, while many of the foregoing examples have focused on playback of stored audio files, in other embodiments, the tablet 1502 or audio device 125 can furthermore apply auditory compensation data to generate compensated audio 1504 in response to streaming audio content, broadcast audio content and/or other audio data.

FIG. 16 presents a flow diagram representation 1600 of a method in accordance with an embodiment of the present invention. In particular, a method is presented for use in conjunction with one or more functions and features presented in conjunction with FIGS. 1-15. Step 1602 includes selecting one of a plurality of audio files in response to user interaction with a graphical user interface. Step 1604 includes decoding the selected one of the plurality of audio files to generate audio output signals for playback of the selected one of the plurality of audio files via an audio output device. Step 1606 includes generating animated auditory system display data in response to the selected one of the plurality of audio files and for display via a display device, wherein the animated auditory system display data animates action of at least one simulated cochlea in response to the selected one of the plurality of audio files.

In various embodiments, the method can further include responding to first user interaction with the graphical user interface to modify a viewing perspective of the at least one simulated cochlea presented by the animated auditory system display data; and responding to second user interaction with the graphical user interface to modify a viewing magnification of the at least one simulated cochlea presented by the animated auditory system display data. The animated auditory system display data can be generated in response to the selected one of the plurality of audio files by: separating the audio output signals into a discrete number of frequency components each having a corresponding component frequency; extracting an amplitude of each frequency component and generating amplitude data based on the amplitude of each frequency component; generating a simulated waveform for each frequency component, based on the amplitude data and a simulated frequency that is different from the component frequency; and simulating the action of the cochlea for each frequency component at a position along the at least one simulated cochlea corresponding to the corresponding component frequency for each frequency component, based on the simulated waveform for each frequency component.

In various embodiments, generating the simulated waveform for each frequency component can be further based on at least one of: hearing test data from a user, hearing compensation data for the user or a prediction of future hearing of the user.

It is noted that terminologies as can be used herein such as bit stream, stream, signal sequence, etc. (or their equivalents) have been used interchangeably to describe digital information whose content corresponds to any of a number of desired types (e.g., data, video, speech, audio, etc. any of which can generally be referred to as 'data').

As can be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As can also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but can adjust its current level, voltage level, and/or power level. As can further be used herein, inferred coupling (i.e., where one element is coupled to another element by inference) includes direct and indirect coupling between two items in the same manner as "coupled to". As can even further be used herein, the term "configured to", "operable to", "coupled to", or "operably coupled to" indicates that an item includes one or more of power connections, input(s), output(s), etc., to perform, when activated, one or more its corresponding functions and can further include inferred coupling to one or more other items. As can still further be used herein, the term "associated with", includes direct and/or indirect coupling of separate items and/or one item being embedded within another item.

As can be used herein, the term "compares favorably", indicates that a comparison between two or more items, signals, etc., provides a desired relationship. For example, when the desired relationship is that signal 1 has a greater magnitude than signal 2, a favorable comparison can be achieved when the magnitude of signal 1 is greater than that of signal 2 or when the magnitude of signal 2 is less than that of signal 1. As can be used herein, the term "compares unfavorably", indicates that a comparison between two or more items, signals, etc., fails to provide the desired relationship.

As can also be used herein, the terms "processing module", "processing circuit", "processor", and/or "processing unit" can be a single processing device or a plurality of processing devices. Such a processing device can be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit can be, or further include, memory and/or an integrated memory element, which can be a single memory device, a plurality of memory devices, and/or embedded circuitry of another processing module, module, processing circuit, and/or processing unit. Such a memory device can be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices can be centrally located (e.g., directly coupled together via a wired and/or wireless bus structure) or can be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions can be embedded within, or external to, the circuitry comprising the state machine, analog circuitry, digital circuitry, and/or logic circuitry. Still further note that, the memory element can store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks can also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram can include a "start" and/or "continue" indication. The "start" and "continue" indications reflect that the steps presented can optionally be incorporated in or otherwise used in conjunction with other routines. In this context, "start" indicates the beginning of the first step presented and can be preceded by other activities not specifically shown. Further, the "continue" indication reflects that the steps presented can be performed multiple times and/or can be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process can include one or more of the aspects, features, concepts, examples, etc. described with reference to one or more of the embodiments discussed herein. Further, from figure to figure, the embodiments can incorporate the same or similarly named functions, steps, modules, etc. that can use the same or different reference numbers and, as such, the functions, steps, modules, etc. can be the same or similar functions, steps, modules, etc. or different ones.

Unless specifically stated to the contra, signals to, from, and/or between elements in a figure of any of the figures presented herein can be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that can include or operate in association with a memory that stores operational instructions. A module can operate independently and/or in conjunction with software and/or firmware. As also used herein, a module can contain one or more sub-modules, each of which can be one or more modules.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. An audio device comprising:
   an audio output interface configured to couple audio signals to an audio output device;
   a graphical user interface including a display device;
   a memory that stores an auditory simulation application;
   a system, including at least one processor, configured by the auditory simulation application to:
      generate animated auditory system display data in response to the audio signals for display via the display device, wherein the animated auditory system display data animates action of a cochlea in response to the audio signals by:
         separating the audio signals into a discrete number of frequency components each having a corresponding component frequency;
         extracting an amplitude of each frequency component and generating amplitude data based on the amplitude of each frequency component;
         generating a simulated waveform for each frequency component, based on the amplitude data and a simulated frequency that is different from the component frequency; and
         simulating action of the cochlea for each frequency component at a position along the cochlea corresponding to the corresponding component frequency for each frequency component, based on the simulated waveform for each frequency component.

2. The audio device of claim 1 wherein the animated auditory system display data further animates action of the cochlea in response to the audio signals by:
   indicating excited regions of the cochlea by changes in color.

3. The audio device of claim 1 wherein simulating the action of the cochlea includes simulating excitation of cochlear nerves by color variations.

4. The audio device of claim 1 wherein the animated auditory system display data is generated by:
   responding to user interaction with the graphical user interface to select one of a plurality of cochlear images;
   wherein the animated auditory system display data is generated further based on the selected one of the plurality of cochlear images.

5. The audio device of claim 4 wherein the plurality of cochlear images includes at least one non-anatomical representation of a spiral structure.

6. The audio device of claim 1 wherein the animated auditory system display data further animates action of the cochlea in response to the audio signals by animating a non-anatomical representation of the cochlea.

7. The audio device of claim 1 wherein the animated auditory system display data further animates action of the cochlea in response to the audio signals by:
   contemporaneously displaying two simulations to indicate a difference in cochlear excitation.

8. The audio device of claim 1 wherein the system is further configured by the auditory simulation application to:
   respond to user interaction with the graphical user interface to select at least one other element of an ear from at least one of: an auditory nerve, an eardrum, or an ear bone;
   wherein the animated auditory system display data animates action of the at least one other element of the ear in response to the audio signals.

9. The audio device of claim 1 wherein the system is further configured by the auditory simulation application to:
   respond to second user interaction with the graphical user interface by modify a viewing perspective of the cochlea presented by the animated auditory system display data; and
   respond to third user interaction with the graphical user interface by modify a viewing magnification of the cochlea presented by the animated auditory system display data.

10. The audio device of claim 1 wherein the system is further configured by the auditory simulation application to:
    respond to second user interaction with the graphical user interface to receive auditory feedback indications from a user of the audio device in response to playback of the audio signals;
    analyze the auditory feedback indications from the user to generate user profile data corresponding to the user that includes hearing test data that indicates hearing of the user; and
    modify the animated auditory system display data based on the user profile data to indicate the hearing of the user.

11. The audio device of claim 10 wherein the system is further configured by the auditory simulation application to:
    generate hearing compensation parameters of the user, based on the user profile data corresponding to the user that indicates the hearing of the user; and
    further modify the animated auditory system display data based on the user profile data to indicate the hearing of the user and the hearing compensation parameters of the user.

12. The audio device of claim 11 wherein the hearing test data is generated for a particular listening environment and the hearing compensation parameters of the user further provide equalization for the particular listening environment.

13. The audio device of claim 11 wherein the system is further configured by the auditory simulation application to:
    modify the hearing compensation parameters of the user based on third user interaction with the graphical user interface to select a level of partial compensation for hearing of the user.

14. The audio device of claim 1 wherein the system is further configured by the auditory simulation application to:
    respond to second user interaction with the graphical user interface to receive hearing test data from a user of the audio output device;
    generate, in response to the hearing test data, user profile data corresponding to the user that indicates hearing of the user; and
    modify the animated auditory system display data based on the user profile data to indicate the hearing of the user.

15. The audio device of claim 1 wherein the system is further configured by the auditory simulation application to:
    respond to second user interaction with the graphical user interface to select a future hearing model for a user of the audio output device; and
    modify the animated auditory system display data based on the future hearing model to indicate a prediction of future hearing of the user.

16. The audio device of claim 1 wherein generating the simulated waveform for each frequency component is further based on hearing test data from a user.

17. The audio device of claim 1 wherein generating the simulated waveform for each frequency component is further based on hearing compensation data for a user.

18. The audio device of claim 1 wherein generating the simulated waveform for each frequency component is further based on a prediction of future hearing of a user.

19. The audio device of claim 1 wherein the system is further configured by the auditory simulation application to:
respond to second user interaction with the graphical user interface to select a level of hearing impairment; and
modify the animated auditory system display data based on the selected level of hearing impairment.

20. A method comprising:
generating animated auditory system display data, wherein the animated auditory system display data animates action of at least one simulated cochlea by:
separating audio signals into a discrete number of frequency components each having a corresponding component frequency;
extracting an amplitude of each frequency component and generating amplitude data based on the amplitude of each frequency component;
generating a simulated waveform for each frequency component, based on the amplitude data and a simulated frequency that is different from the component frequency; and
simulating the action of the at least one simulated cochlea for each frequency component at a position along the at least one simulated cochlea corresponding to the corresponding component frequency for each frequency component, based on the simulated waveform for each frequency component.

* * * * *